United States Patent [19]
Balaban et al.

[11] Patent Number: 5,304,119
[45] Date of Patent: Apr. 19, 1994

[54] INSTRUMENT FOR INJECTING IMPLANTS THROUGH ANIMAL HIDE

[75] Inventors: Stephen M. Balaban, Chesterfield; Jonathan P. Smith, Pacific, both of Mo.

[73] Assignee: Monsanto Company, St. Louis, Mo.

[21] Appl. No.: 80,857

[22] Filed: Jun. 24, 1993

[51] Int. Cl.$^5$ .................. A61M 31/00; A61M 29/00; A61M 16/00
[52] U.S. Cl. ........................ 604/51; 604/64; 604/107; 606/108
[58] Field of Search ............... 604/57, 59–64, 604/104–109, 51, 158, 160, 204, 272, 274; 606/108, 109

[56] References Cited

U.S. PATENT DOCUMENTS

| | | | |
|---|---|---|---|
| 2,017,783 | 10/1935 | Clark | 604/63 |
| 2,201,749 | 5/1940 | Vandegrift | 604/107 X |
| 2,269,963 | 1/1942 | Wappler | 604/62 X |
| 2,842,133 | 7/1958 | Uhma | 606/108 |
| 3,611,965 | 12/1971 | Lange | 604/160 |
| 3,682,173 | 8/1972 | Center | |
| 3,877,429 | 4/1975 | Rasumoff | |
| 3,934,584 | 1/1976 | Corio | 604/59 |
| 4,068,659 | 1/1978 | Moorehead | |
| 4,211,234 | 7/1980 | Fisher | 606/108 X |
| 4,287,892 | 9/1981 | Schiff | |
| 4,377,165 | 3/1983 | Luther et al. | |
| 4,402,685 | 9/1983 | Bühler et al. | 604/175 |
| 4,447,237 | 5/1984 | Frisch et al. | 604/175 |
| 4,449,973 | 5/1984 | Luther | 604/161 |
| 4,490,136 | 12/1984 | Ekbladh et al. | 604/22 |
| 4,537,593 | 8/1985 | Alchas | 604/411 |
| 4,545,367 | 10/1985 | Tucci | |
| 4,548,210 | 10/1985 | Enjoji et al. | 128/660 |
| 4,565,544 | 1/1986 | Müller et al. | 604/164 |
| 4,655,752 | 4/1987 | Honkanen et al. | 604/256 |
| 4,716,901 | 1/1988 | Jackson et al. | |
| 4,735,215 | 4/1988 | Goto et al. | 128/754 |
| 4,753,641 | 6/1988 | Vaslow | 604/274 |
| 4,781,693 | 11/1988 | Martinez et al. | 604/175 |
| 4,846,793 | 7/1989 | Leonard et al. | 604/62 |
| 4,863,430 | 9/1989 | Klyce et al. | 604/164 |
| 4,921,479 | 5/1990 | Grayzel | 604/53 |
| 5,006,113 | 4/1991 | Fischer | 604/167 |
| 5,081,985 | 1/1992 | Borodulin et al. | 128/32 |

FOREIGN PATENT DOCUMENTS

| | | | |
|---|---|---|---|
| 37519 | 5/1927 | Denmark. | |
| 0378095 | 7/1990 | European Pat. Off. | |
| 2524309 | 10/1983 | France | 604/60 |
| 8901281 | 12/1990 | Netherlands | 604/60 |
| 0632812 | 12/1949 | United Kingdom | 604/59 |

OTHER PUBLICATIONS

Irving Silverman, New Biopsy Needle, (date unknown), pp. 671–672.
California Medicine, The Western Journal of Medicine, vol. 117, No. 2, pp. 22, 23, and 24 (date not known).

Primary Examiner—John D. Yasko
Assistant Examiner—Adam J. Cermak
Attorney, Agent, or Firm—Gary M. Bond; George R. Beck

[57] ABSTRACT

An instrument for injecting implants through animal hide is comprised of an injector having a tubular body divided into two adjacent segments with a hollow interior bore extending through the segments of the body. The second segment of the body has a generally tapering configuration as it extends to the distal end of the body and is formed as a pair of laterally adjacent tines that extend longitudinally from adjacent the first body segment to the distal end of the body. One of the tines has a larger lateral width than a second of the tines at laterally adjacent cross sections of the tines, and one tine has a terminal end at the distal end of the body for making incisions through animal hide when employing the instrument in injecting implants. A push rod having a longitudinal length at least equal to the longitudinal length of the body is inserted through the interior bore of the body pushing the implant before it. As the push rod passes through the interior it forces the pair of tines radially away from each other thereby dilating the incision, and the push rod injects the implant into the livestock as a distal end of the push rod reaches the distal end of the body.

20 Claims, 2 Drawing Sheets

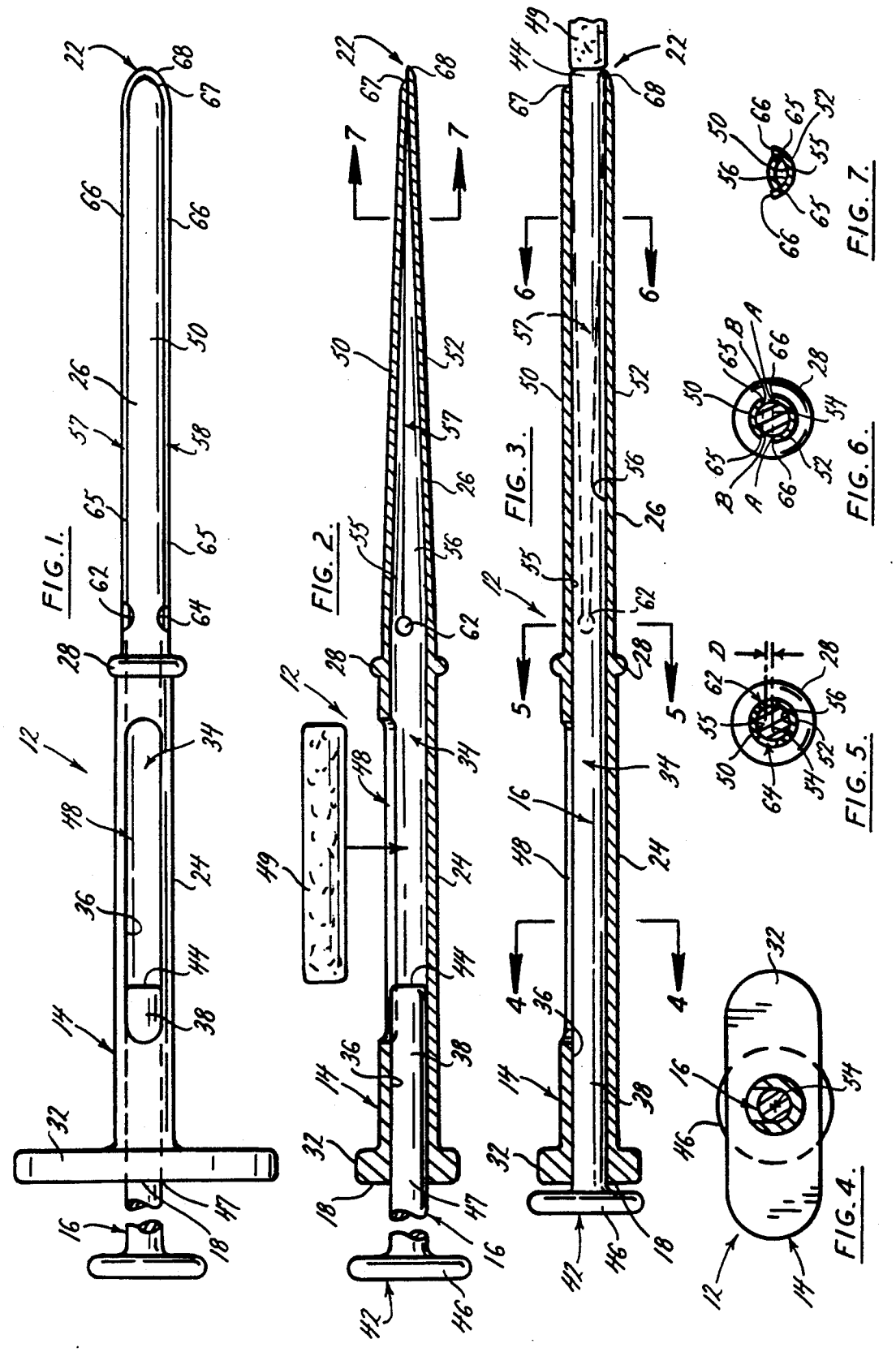

INSTRUMENT FOR INJECTING IMPLANTS THROUGH ANIMAL HIDE

BACKGROUND OF THE INVENTION

(1) Field of the Invention

The present invention pertains to an instrument for subcutaneously, intramuscularly, or intraperitoneally injecting implants through animal hide wherein the instrument is comprised of a tubular injector body and a push rod dimensioned to be inserted longitudinally through an interior bore of the injector body. The injector body is formed with a pair of laterally spaced tines at one end with one of the tines projecting longitudinally beyond the second of the tines and presenting an incising tip that facilitates piercing the hide prior to insertion of the tines beneath the hide.

(2) Description of the Related Art

Prior art methods of inserting implants or substances into animals subcutaneously, intermuscularly, or interperitoneally typically require that an incision be made that permits the implant to be injected through the incision. Use of a tubular trocar or a large needle would at times result in a core of flesh or hide of the animal being formed in the piercing end of the trocar as it is inserted through the animal's hide. As the implant is pushed through the interior of the trocar to be deposited in the animal, the core of flesh or hide is pushed before the implant into the animal and is deposited with the implant. This prior art method of inserting implants presented the danger of causing infection of the animal by bacteria on the surface of the core of flesh or hide deposited inside the animal with the implant.

To reduce the occurrence of flesh or hide coring in inserting implants into animals, prior art trocars were developed with a solid cutting edge at the piercing tip of the trocar. The solid cutting edge was provided by an insert such as a solid pointed probe that was pushed down through the interior of the needle or trocar to a position where the point of the insert projects just beyond the piercing tip of the trocar. The trocar and the pointed insert received in the trocar were then inserted together through the animal hide and into the animal. Following insertion, the solid insert was withdrawn from the interior of the trocar leaving a pathway through the trocar for the insertion of implants into the animal.

Fine gauge needles having solid points and outlet ports on their sides have also been employed in the delivery of medicament into animals. With these types of needles the medicament is delivered, or a sample is taken, through the side passageway of the needle.

The insertion of implants into animals where the implants have a significantly large diameter has grown in importance as capsulized sustained release substances, such as medicaments or growth agents, have been developed. However, inserting such implants by the prior art method of employing a trocar or large needle have been found to be disadvantaged in that the core of flesh or hide carried into the animal with the insert often leads to infections and abscesses and at times a rejection of the implant. The prior art method of employing a hollow trocar with a solid cutting edge insert pushed through the interior of the trocar has also been found to be disadvantaged in that it is often important that the implant be quickly administered and the quick administration of the implant does not allow time for use of the solid point trocar device. Prior art fine gauge needles typically do not have interior bore dimensions of sufficient size to accommodate capsulized implants.

Prior art devices have been developed in efforts to form an opening through the hide for introducing tubing and other similar apparatus into animals. Typical of these prior art apparatus is the surgical appliance disclosed in U.S. Pat. No. 4,716,901 to Jackson et al. The appliance is generally comprised of a trocar and an expander. The trocar is tubular and is divided into two components by diametrically opposed longitudinally extending cut away openings. Each of the openings taper inwardly from the distal end to the proximal end of the tube and the shape of the openings results in the formation of two trocar components which, at their distal ends, subtend only small angles around the longitudinal axis of the trocar tube. The distal extremities of the two components are adapted to provide a point for piercing the skin in their fully closed condition. The expander comprises a thin tube shorter than the trocar, with an interior bore just large enough to allow a drain tube to slide easily therethrough.

In use of the Jackson et al. appliance, the distal ends of the trocar components pierce the skin and an incision is made by the cutting edges of the components. The end portion of the trocar is then passed through the skin. The expander tube is inserted into the trocar and is passed through the bore of the trocar. The advancing movement of the expander forces the trocar components apart to their fully opened condition, and a drain tube is slid through the expander and the open forward portions of the trocar components. Finally, the trocar and the expander are withdrawn from the incision over the length of the drain tube and the skin stretched by the opening of the trocar contracts on the drain tube gripping it in place.

Although appliances of the type described in the Jackson et al. patent represent advancements over the prior art, they still leave room for improvement when using such devices for the subcutaneous, intermuscular, or interperitoneal injection of implants through animal hide. The incising tip of such devices typically is not specifically designed to produce a single slit incision through the animal hide prior to insertion of the appliance. The trocar components typically are not designed to present as small a cross sectional area as possible of the appliance pushed through the slit incision to facilitate insertion of the components through the incision.

SUMMARY OF THE INVENTION

The instrument of the present invention overcomes the disadvantages associated with prior art implant inserting devices by providing an instrument that makes only a small slit incision in the animal's hide when employed in inserting implants, and then dilates after insertion presenting an interior bore of the instrument dimensioned sufficiently large to permit the delivery of implants of significant diameter.

The instrument of the invention is generally comprised of a tubular body and a plunger rod. The tubular body has a pair of longitudinally extending slots cut through the body adjacent its distal end. The slots are positioned on opposite sides of the body but are not diametrically opposite each other as are the slots in prior art appliances such as that disclosed in U.S. Pat. No. 4,716,901. Each slot extends from the distal end of the body to almost a midpoint of the body and has an extended triangular configuration with the base of the triangle positioned adjacent the distal end of the body and the apex positioned at the termination of the slot near the midpoint of the body.

The pair of slots form two elongated tines at the distal end of the tubular body. Each of the tines has a generally arcuate cross section and one of the tines has a smaller width and shorter length than the other of the two tines due to the slots being formed in the tubular body at positions not diametrically opposite each other. The arcuate cross section of the tines gives their mutually opposed interior surfaces the configurations of curved grooves. The two tines are resilient and biased inward toward each other and toward the center axis of the body with the smaller tine engaging inside the concave or curved groove of the larger tine. The tip of the smaller tine nests within the curved groove of the larger tine so that only the tip of the larger tine is presented as the incising tip of the instrument. The relative positioning of the two tips of the tines at the distal end of the trocar enables the tines to be easily inserted through livestock hide making only a narrow slit incision through the hide by the one longer tine. The nesting of the shorter tine within the grooved interior surface of the longer tine reduces the cross sectional area of the instrument inserted through the incision than that of prior art devices such as that disclosed in U.S. Pat. No. 4,716,901, thereby facilitating its insertion. An oblong opening is provided in a lateral side of the tubular body adjacent its proximal end. The opening is provided to receive capsulized substances in the interior of the tubular body for injection into the livestock.

The plunger rod has an exterior diameter dimensioned just slightly smaller than the interior diameter of the tubular body and has a longitudinal length substantially equal to that of the body. As the plunger is inserted into the interior bore of the body from the proximal end opposite the tines, the end of the plunger passes by the oblong opening and pushes down the length of the bore an implant inserted into the bore through the oblong opening. As the plunger is advanced toward the tines at the distal end of the body the end of the plunger engages against the concave grooved interior surfaces of the tines and forces them apart, thereby dilating the incision. The movement of the tines radially away from each other provides an opening through the incision in the livestock hide that enables insertion of the capsulized implant pushed before the plunger into the body of the livestock. In this manner the instrument of the invention enables the insertion of implants into animals subcutaneously, intermuscularly, or interperitoneally without the occurrence of coring of the animal hide as was present in the prior art, without the time consuming steps involved in employing the prior art trocar with the solid cutting edge insert, and by making only a single slit incision through the animals hide and by facilitating the insertion of the instrument through the incision.

BRIEF DESCRIPTION OF THE DRAWINGS

Further objects and features of the present invention are revealed in the following detailed description of the preferred embodiment of the invention and in the drawing figures wherein:

FIG. 1 is a segmented plan view of the injection instrument of the present invention;

FIG. 2 is a segmented side elevation view, in section, of the instrument of the invention;

FIG. 3 is a side elevation view, in section, of the instrument of the invention;

FIG. 4 is a front elevation view, in section, taken along the line 4—4 of FIG. 3;

FIG. 5 is a front elevation view, in section, taken along the line 5—5 of FIG. 3;

FIG. 6 is a front elevation view, in section, taken along the line 6—6 of FIG. 3;

FIG. 7 is a rear elevation view, in section, taken along the line 7—7 of FIG. 2.

DETAILED DESCRIPTION OF THE PREFERRED EMBODIMENT

Figure 8:
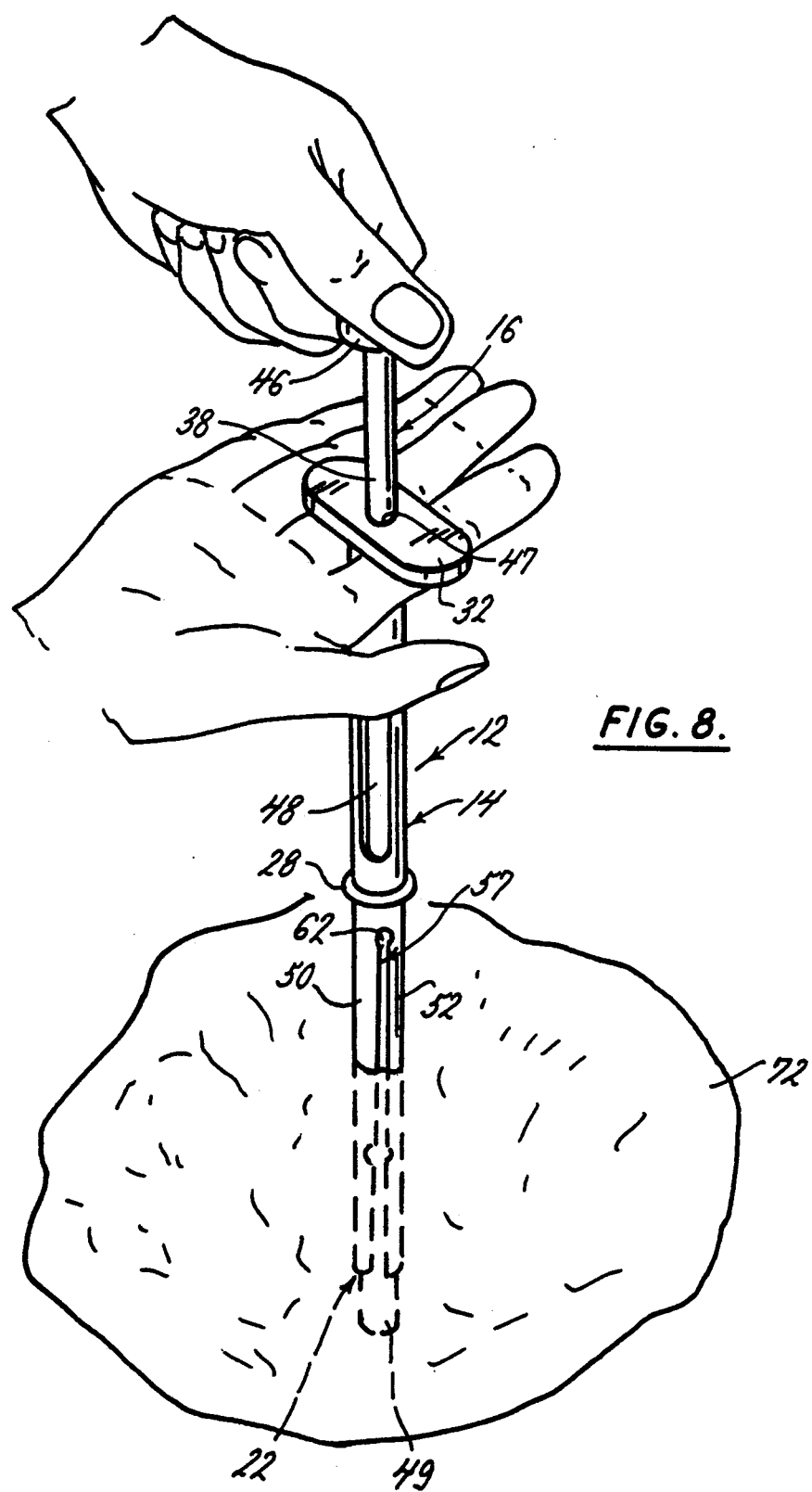
FIG. 8 is a perspective view of use of the instrument in one operative embodiment.

FIG. 1 shows the injection instrument 12 of the present invention. The preferred embodiment of the instrument is employed in performing subcutaneous, intermuscular, or interperitoneal injections of implants or capsulized substances into livestock, although other uses may be made of the instrument. The instrument is generally comprised of an injector 14 and a push rod 16. In the preferred embodiment of the invention both the injector 14 and push rod 16 are constructed entirely of metal by conventional metal forming processes. However, the two basic component parts of the invention may be constructed of other materials and by other methods without departing from the intended scope of the invention.

As best seen in FIG. 3, the injector 14 is comprised of a tubular body having longitudinally opposite first 18 and second 22 ends. The body is subdivided into a first segment 24 adjacent the body first end and a second segment 26 adjacent the body second end with the first and second segments being separated by an annular hilt 28 that surrounds the body. A T-shaped handle 32 is also formed on the first segment 24 at the body first end 18. Except for the annular hilt 28 and T-shaped handle 32 formed on the exterior surface of the injector body, the body exterior surface has a generally cylindrical configuration between the first end 18 and second end 22.

A hollow interior bore 34 extends longitudinally through the injector body between the first and second ends 18, 22. The bore is surrounded by an interior wall 36 of the body. The interior wall 36 has a generally cylindrical configuration as shown in FIG. 3.

The push rod 16 is comprised of an elongated, cylindrical rod 38 having opposite first 42 and second 44 ends with a circular head 46 formed on the first end of the rod. As seen in FIG. 3, the rod 38 has a longitudinal length substantially equal to that of the injector body interior bore 34. The rod 38 has a cross section diameter slightly smaller than the cross section diameter of the injector body interior bore 34 to enable the rod to slide freely through the interior bore.

The first segment 24 of the injector body 14 is provided with a pair of openings to facilitate the use of the instrument in performing implant injections. The interior bore 34 of the injector exits through the injector first end 18 and forms a first opening 47 for insertion of the second end 44 of the push rod therein. A second, oblong access opening 48 is provided extending laterally through the side of the body first segment 24. The access opening 48 is given a longitudinally oblong configuration to permit the insertion of a variety of different sized implants 49 into the injector body interior 34 through the opening. As seen in FIG. 4, the lateral width of the access opening 48 is substantially equal to the diameter of the interior bore 34. This allows implants 49 having diameter dimensions slightly smaller than that of the interior bore 34 to be inserted into the bore.

The second segment 26 of the injector body is formed as a pair of resilient tines 50, 52 having curved or arcuate cross sections. The resiliency of the tines biases them toward a center axis 54 of the injector body to first relative positions of the tines shown in FIG. 2. The arcuate cross sections of the tines gives the tines curved, mutually opposed interior surfaces 55, 56. The curvature of the tines' interior surfaces forms curved grooves extending longitudinally along the lengths of the tines. Insertion of the push rod 16 through the body interior bore forces the tines 50, 52 radially apart from each other to second relative positions of the tines shown in FIG. 3. With the tines in their second relative positions the entire longitudinal length of the injector body has a generally cylindrical exterior surface and a generally cylindrical interior surface. With the push rod 16 retracted from the portion of the interior bore 34 extending through the second segment 26 of the injector body, the resiliency of the tines 50, 52 biases the tines toward the center axis 54 of the body to the first relative positions of the tines shown in FIG. 2, where the tines engage each other with at least a portion of one tine 50 nesting within the groove 56 formed by the interior surface of the other tine 52.

Each of the tines 50, 52 are formed by a pair of slots 57, 58 in the second segment 26 of the injector body. The slots extend longitudinally through the body second segment 26 from the second end 22 of the body to a pair of apertures 62, 64 formed in opposite lateral sides of the body second segment 26 adjacent the hilt 28. The slots each have a general triangular configuration with the triangle base adjacent the body second end 22 and the triangle apex at the apertures. Each of the slots 57, 58 are substantially identical and, as best seen in FIG. 3, taper as they extend from the body second end 22 to their respective apertures 62, 64.

Although the slots 57, 58 and their respective apertures 62, 64 are formed through opposite lateral sides of the body second segment 26, they are not positioned diametrically opposite to each other as are the slots in prior art devices such as that disclosed in U.S. Pat. No. 4,716,901. As seen in the cross section of FIG. 6, the slots 57, 58 do not bisect the body second segment 26 but are offset from the center axis 54 of the injector body. The lateral line A—A represents a diameter of the injector interior bore and, as seen in FIG. 6, the slots 57, 58 are not centered at opposite ends of a diameter but are centered at opposite ends of a chord B—B which is offset from the diameter A—A and the center axis 54 of the bore by a radial distance D. As best seen in FIG. 5, the apertures 62, 64 have a common lateral axis that is radially offset from the injector body center axis 54 by the same distance D.

The tapering configuration of the slots 57, 58 as they extend from the body second end 22 to their respective apertures 62, 64 gives the pair of tines 50, 52 formed by the slots tapering configurations. The pair of slots 57, 58 form each of the tines 50, 52 with opposite lateral side edges 65, 66, respectively, that taper toward each other and converge at rounded terminal ends 67, 68 of the respective tines. As best seen in FIGS. 5-7, the offset distance D of the slots 57, 58 from the injector body center axis 54 causes the lateral width and arc formed by the cross section of one tine 52 to be larger than the lateral width and arc formed by the cross section of the second tine 50 for laterally adjacent cross sections of the tines along their entire longitudinal lengths. This difference in the lateral widths of the tines allows the second tine 50 to be completely received within the lateral width dimension of the one tine 52 as the tines extend toward the second end 22 of the injector body. As is best seen in FIG. 1, the specific configuration of the tines provided by the positioning of the slots enables the laterally opposite side edges 65 of the second tine 50 to nest within the curved groove 56 formed by the interior surface of the one tine 52. The laterally opposite side edges 66 and adjacent portions of the interior surface of the one tine 52 extend around and overlap the laterally opposite side edges 65 of the second tine 50. As seen in FIG. 7, with the push rod 16 removed from the body interior, the configuration of the tines 50, 52 enables them to occupy a smaller cross sectional area than if the tines had equal lateral widths. With tines of equal lateral widths the opposite lateral edges of the tines would engage against each other and prevent one tine from nesting within the groove formed by the interior surface of the other tine. The concave interior surfaces of the tines allows the terminal end 67 of the second tine 50 to be received within a portion of the groove 56 formed by the curved interior surface of the one tine 52 and to engage against the curved surface. This reduction in the cross sectional area of the tines facilitates their insertion through an incision in an animal's hide in performing injections of implants into livestock with the instrument of the invention.

The lateral positioning of the slots 57, 58 and the difference in tine widths resulting therefrom also causes the second tine 50 to taper and converge to its rounded terminal end 67 before the one tine 52 tapers and converges to its rounded terminal end 68. This results in the one tine terminal end 68 being positioned at the body second end 22, where the second tine terminal end 67 is spaced longitudinally from the one tine terminal end and the body second end 22. With this configuration, only the terminal end 68 of the one tine is presented as the cutting or incising tip of the instrument which makes the initial incision through livestock hide when the instrument is employed in injection procedures. The single cutting edge at the terminal end 68 of the one tine 52 presents a much sharper cutting edge for making incisions than would the pair of adjacent cutting tips should both tines have the same longitudinal length.

In use of the instrument of the invention 12 in injections of implants into livestock, the push rod 16 is first retracted through the body interior bore 34 to the positions of the push rod and body shown in FIGS. 1 and 2. In these relative positions both the injector body and push rod may be easily held in one hand by the user. With the push rod and body held in one hand, the other hand of the user may easily insert an implant 49 through the access opening 48 and into the interior bore 34 of the body in front of the second end 44 of the push rod.

With the implant 49 contained in the body interior 34, the terminal end 68 of the one tine 52 is used as a cutting edge to pierce the animal hide in initial insertion of the body second end 22 through the animal hide. The initial incision made through the animal hide has the configuration of an arcuate line with the opposed edges of the animal hide cut by the tip of the one tine 52 forming the arcuate line. As the body second end 22 is continued to be inserted through the animal hide, the incision through the hide expands around the lateral side edges 66 of the one tine 52. The length of the incision between its opposite ends increases as the one tine end 68 is inserted into the incision. The one side of the incision engaging against the exterior surface of the one tine 52 maintains its arcuate configuration while the opposite side of the incision is stretched across the lateral edges 66 of the tine, giving the incision a configuration of a circle segment. The terminal end 67 of the second tine 50, being positioned within the curved groove 56 of the one tine 52, passes easily through the circle segment configuration of the incision. The reduced cross sectional area of the body second segment 26 facilitates the insertion of the body segment beneath the animal hide. The second segment 26 is continued to be inserted through the incision and may be inserted to the extent that the incision passes entirely over the second segment 26 to a position adjacent the hilt 28. If the second segment 26 is inserted to the hilt 28, the configuration of the incision will expand from the circle segment configuration to the configuration of a full circle.

The length of body second segment 26 can vary depending on the type of implantation (subcutaneous, intramuscular, or intraperitoneal), the species, the breed, and even the age or sex if an animal, and the like. For example, for intraperitoneal implants, trocar lengths of 2", 2¼" and 3" were satisfactory for implantation via the left para lumbar fossa of crossbred steers, while 2¼" was recommended for avoiding possible internal damage.

With the body second segment 26 completely inserted to the desired extent beneath the animal hide 72 as shown in FIG. 8 (less than full insertion to the hilt 28), the user of the instrument then advances the push rod 16 longitudinally through the interior-bore 34 of the injector body toward the body second end 22. The user pushes the rod head 46 toward the body handle thereby moving the rod second end 44 through the interior bore and pushing the implant 49 through the bore before the rod second end 44. As the implant 49 and the rod second end 44 pass through the portion of the interior bore extending through the second segment 26, the implant 49 and the second end of the push rod 44 force the tines 50, 52 radially away from each other against their resilient bias, thereby dilating or expanding the incision to a full circle configuration. The implant 49 and push rod 16 are continued to be pushed longitudinally through the interior bore 34 until the rod second end 44 is positioned adjacent the injector body second end 22 and the implant 49 exits the body second end and is injected into the body of the livestock. At this point the relative positions of the rod second end 44, the implant 49, and the pair of tines 50, 52 are as shown in FIG. 3. In FIG. 3 the tines 50, 52 are positioned in their second relative positions, spaced radially from each other and from the body center axis 54 to their furthest extent and the entire longitudinal length of the injector body assumes a generally cylindrical configuration.

Following insertion of the implant 49, the instrument 12 is removed from the incision and the rod 16 is removed from the interior bore 34 of the injector body. As the rod second end 44 is moved longitudinally from the interior bore portion extending through the second segment 26 of the body, the resiliency of the tines 50, 52 biases the tines radially toward each other until the tines engage and assume their first relative positions shown in FIG. 2.

While the present invention has been described by reference to a specific embodiment, it should be understood that modifications and variations of the invention may be constructed without departing from the scope of the invention defined in the following claims.

What is claimed is:

1. An injection instrument comprising:
   an injector having a tubular body with longitudinally opposite first and second ends, the body having at least two longitudinally adjacent coaxial segments and a hollow interior bore extending longitudinally through the body between the first and second ends;
   the first segment of the body being adjacent the body first end;
   the second segment of the body being adjacent the body second end and having a generally tapering configuration toward the body second end, the second segment of the body being formed as a pair of laterally adjacent tines that extend longitudinally from adjacent the body first segment to the body second end, each of the tines has laterally opposite side edges that converge toward each other as the tines extend longitudinally from adjacent the body first segment toward the body second end, the pair of tines have mutually opposed interior surfaces between their laterally opposite side edges, and the laterally opposite side edges and portions of the interior surface of one tine of the pair extend around and overlap the laterally opposite side edges of a second tine of the pair; and,
   a push rod having opposite first and second ends and an exterior configuration that enables the push rod to be inserted through the interior bore of the injector body to the body second end and force the pair of tines radially away from each other for pushing an implant through the interior bore before the push rod and out the body second end.

2. The instrument of claim 1, Wherein:
   the one tine of the pair has a terminal end at the second end of the body and the second tine of the pair has a terminal end spaced longitudinally from the second end of the body and the terminal end of the one tine; and
   each of the tines have curved cross-sectional configurations with mutually opposed concave interior surfaces and the terminal end of the second tine is received within a portion of the body interior bore bounded by the curved interior surface of the one tine.

3. The instrument of claim 1, wherein:
   the one tine of the pair has a terminal end at the second end of the body and the second tine of the pair has a terminal end spaced longitudinally from the second end of the body and the terminal end of the one tine; and,
   each of the tines have curved cross-sectional configurations with mutually opposed concave interior surfaces and the terminal end of the second tine engages against the interior surface of the one tine.

4. The instrument of claim 1, wherein:
   each of the tines has a curved cross-sectional configuration with each of the mutually opposed interior surfaces of the tines forming a curved groove that extends longitudinally along the tine, and the laterally opposite side edges of the second tine nest within the curved groove formed by the interior surface of the one tine.

5. The instrument of claim 1, wherein:

the pair of tines are formed in the second segment of the body by a pair of slots provided in the second segment, the pair of slots extend longitudinally through the second segment from adjacent the first segment to the second end of the body, and the pair of slots are positioned on laterally opposite sides of the second segment where, in a cross section of the second segment, the slots are not diametrically opposite each other, thereby forming the one tine with a larger lateral width than the second tine as the pair of tines extend toward the body second end.

6. The instrument of claim 5, wherein:

each of the slots has a tapered shape as the slots extend from the second end of the body to a termination of the slots adjacent the body first section, and each of the tines is resilient whereby resiliency of the tines biases the tines toward each other causing the terminal end of the second tine to engage against the one tine.

7. The instrument of claim 6, wherein:

inserting the second end of the push rod into the interior bore of the injector body and pushing the rod second end through the bore from the first end of the body toward the second end of the body causes the rod second end to engage against the pair of tines and push the pair of tines radially away from each other, and pulling the second rod end through the interior bore toward the first end of the body causes the rod second end to disengage from the pair of tines and allows the resiliency of the tines to bias the tines radially back toward each other.

8. The instrument of claim 1, wherein:

an opening is provided in the first segment of the body extending laterally through the first segment to the interior bore, the opening provides access to the interior bore whereby an object may be inserted laterally through the opening and into the interior bore and then pushed longitudinally through the bore by the push rod being inserted through the bore.

9. An injection instrument comprising:

an injector having a tubular body with longitudinally opposite first and second ends, the body having at least two longitudinally adjacent coaxial segments and a hollow interior bore with a center axis extending longitudinally through the body between the first and second ends;

the first segment of the body being adjacent the body first end and having a generally cylindrical exterior surface and a generally cylindrical interior surface surrounding a first portion of the interior bore extending through the first segment of the body;

the second segment of the body being adjacent the body second end and having a generally tapering exterior surface as the second segment extends from the first segment toward the body second end, the second segment of the body being formed as a pair of laterally adjacent tines that taper toward the center axis of the injector body as the tines extend longitudinally from adjacent the body first segment toward the body second end, with one of the tines having a larger lateral width than a second of the tines at laterally adjacent cross sections of the pair of tines as the pair of tines extend toward the body second end; and, a push rod having opposite first and second ends and an exterior surface configured to enable the push rod to be inserted through the interior bore of the injector body and push the pair of tines radially away from the bore center axis.

10. The instrument of claim 9, wherein:

each tine of the pair of tines is formed with laterally opposite side edges that taper toward each other and converge at a terminal end of the tine as the pair of tines extend longitudinally toward the second end of the injector body, and the laterally opposite side edges of the second tine are spaced laterally between the laterally opposite side edges of the one tine.

11. The instrument of claim 9, Wherein:

each of the tines has laterally opposite side edges that converge toward each other as the tines extend longitudinally from adjacent the body first segment toward the body second end, the pair of tines have mutually opposed interior surfaces between their laterally opposite side edges, and the laterally opposite side edges and portions of the interior surface of one tine of the pair extend around and overlap the laterally opposite side edges of a second tine of the pair.

12. The instrument of claim 9, wherein:

the tines each have curved cross-sectional configurations with mutually opposed interior surfaces of the tines forming curved grooves that extend longitudinally along the tines, and the second tine nests within the curved groove formed by the interior surface of the one tine.

13. The instrument of claim 9, wherein:

the pair of tines are separated by a pair of slots formed in the second segment of the body, the pair of slots extend longitudinally through the second segment of the body from adjacent the first segment to the body second end, and the pair of slots are positioned on opposite lateral sides of the second segment where the slots are not diametrically opposite each other, thereby forming the one tine with a larger lateral width than the second tine at laterally adjacent cross sections of the pair of tines.

14. The instrument of claim 13, wherein:

each of the slots has a generally triangular shape defined by opposed deleted side edges of the pair of tines with an apex of each slot being positioned adjacent the injector body first segment and a base of each slot being positioned at the body second end, and each of the tines is resilient whereby resiliency of the tines biases the tines to a first relative position of the tines where the tines engage with each other, from a second relative position of the tines where the tines are spaced radially from the center axis of the injector body.

15. The instrument of claim 14, wherein:

inserting the second end of the push rod into the interior bore of the injector body and pushing the rod second end through the bore from the first end of the body toward the body second end causes the rod second end to engage against the pair of tines and push the pair of tines from their first relative position to their second relative position, and pulling the second rod end through the interior bore toward the body first end causes the rod second end to disengage from the pair of tines and allows the resiliency of the tines to bias the tines back to their first relative position.

16. The instrument of claim 9, wherein:

the hollow interior bore extends axially through the first end of the injector body forming a first opening through the body first segment to the interior bore, and a second opening is provided in the body first segment extending laterally from the exterior surface through the first segment to the interior bore, the second opening providing access to the interior bore whereby an object may be inserted laterally through the second opening and into the interior bore and then pushed longitudinally through the bore by the second end of the push rod being inserted through the first opening and through the interior bore.

17. An injection instrument comprising:

an injector having a tubular body of a longitudinal length with opposite first and second ends, the body having at least two longitudinally adjacent, coaxial segments and a hollow interior bore extending longitudinally through the body between the first and second ends;

the first segment of the body being adjacent the body first end and having a generally cylindrical exterior surface and a first portion of the interior bore having a generally cylindrical interior surface extending through the first segment of the body;

the second segment of the body being adjacent the body second end and having a generally tapering configuration as the second segment extends longitudinally from adjacent the first segment toward the body second end, the second segment of the body being formed as a pair of laterally adjacent tines that extend longitudinally from adjacent the body first segment to the body second end with one tine of the pair having a larger lateral width than a second tine of the pair at laterally adjacent cross sections of the pair of tines as the pair of tines extend toward the body second end, the tines each have curved cross-sectional configurations with mutually opposed interior surfaces of the tines forming curved grooves that extend longitudinally along the tines, the second tine nests within the curved groove formed by the interior surface of the one tine; and, a push rod having opposite first and second ends and a longitudinal length at least equal to the longitudinal length of the body, and the push rod having an exterior configuration that enables the push rod to pass through the interior bore of the body and force the pair of tines radially away from each other as the push rod passes through the interior bore.

18. The instrument of claim 17, wherein:

each of the tines has laterally opposite side edges that converge toward each other as the tines extend longitudinally from adjacent the body first segment toward the body second end, the pair of tines have mutually opposed interior surfaces between their laterally opposite side edges, and the laterally opposite side edges and portions of the interior surface of one tine of the pair extend around and overlap the laterally opposite side edges of a second tine of the pair.

19. The instrument of claim 17, wherein:

the hollow interior bore extends axially through the first end of the injector body forming a first opening through the body first segment to the interior bore, and a second opening is provided in the body first segment extending laterally from the exterior surface through the first segment to the interior bore, the second opening providing access to the interior bore whereby an object may be inserted laterally through the second opening and into the interior bore and then pushed longitudinally through the bore by the second end of the push rod being inserted through the first opening and through the interior bore.

20. A method of subcutaneously, intramusculary, and intraperitoneally injecting implants into animals, the method comprising:

making an incision through an animal's hide where the incision has a configuration of an arcuate line with opposite ends, the arcuate line being formed by opposed edges of the animal hide cut in making the incision;

dilating the incision by first causing a length of the incision between its opposite ends to increase and by causing the configuration of the incision to change from that of an arcuate line to that of a circle segment;

opening a hollow bore through which an implant can be passed and further dilating the incision by causing the configuration of the incision to change from that of a circle segment to that of a full circle;

injecting the implant into the animal by passing the implant through the open hollow bore and the incision with the incision having the configuration of a circle; and, closing the incision to an arcuate configuration of the incision following injection of the implant.

* * * * *